(12) United States Patent
Kurihara et al.

(10) Patent No.: US 6,664,113 B2
(45) Date of Patent: Dec. 16, 2003

(54) FLUORESCENCE DETECTION METHOD CAPABLE OF MAKING MEASUREMENT UNDER EXTERNAL LIGHT

(75) Inventors: Yoshifumi Kurihara, Ebina (JP); Toshinori Hayashi, Sagamihara (JP); Juichi Saitoh, Yamato (JP); Takahiko Ishiguro, Yokohama (JP)

(73) Assignee: Tosoh Corporation, Shinnanyo (JP)

( * ) Notice: Subject to any disclaimer, the term of this patent is extended or adjusted under 35 U.S.C. 154(b) by 9 days.

(21) Appl. No.: 10/126,629

(22) Filed: Apr. 22, 2002

(65) Prior Publication Data

US 2002/0155619 A1 Oct. 24, 2002

(30) Foreign Application Priority Data

Apr. 23, 2001 (JP) ........................................ 2001-124172

(51) Int. Cl.[7] .............................................. G01N 21/64
(52) U.S. Cl. ........................ 436/172; 436/174; 436/180
(58) Field of Search ................................ 436/172, 174, 436/180; 250/458.1, 459.1; 356/36, 246

(56) References Cited

U.S. PATENT DOCUMENTS

| | | |
|---|---|---|
| 4,406,457 A | 9/1983 | Gabrius et al. |
| 5,178,833 A | 1/1993 | Covain |
| 5,376,336 A * | 12/1994 | Lubbers et al. .......... 422/82.06 |
| 5,500,536 A | 3/1996 | Nogami et al. |
| 5,811,312 A * | 9/1998 | Hasegawa et al. .......... 436/527 |
| 5,917,592 A | 6/1999 | Skiffington |
| 6,359,284 B1 | 3/2002 | Hayashi et al. |
| 6,396,581 B1 * | 5/2002 | Hayashi et al. .............. 356/318 |
| 6,515,743 B1 * | 2/2003 | Hayashi et al. .............. 356/317 |

FOREIGN PATENT DOCUMENTS

| | | |
|---|---|---|
| DE | 245 491 | 5/1987 |
| EP | 0 580 362 | 1/1994 |
| EP | 1 087 222 | 3/2001 |
| JP | 2000-214090 | 8/2000 |
| JP | 2001-88752 | 4/2001 |
| JP | 2001-91463 | 4/2001 |
| WO | WO 83/03900 | 11/1983 |

OTHER PUBLICATIONS

P. Harms, et al., Review of Scientific Instruments, vol. 70, No. 2, pp. 1535–1539, XP–000875381, "Low Cost Phase–Modulation Measurements of Nanosecond Fluorescence Lifetimes Using a Lock–in Amplifier", Feb., 1999.

M. C. Moreno–Bondi, et al., Analytical Chemistry, vol. 62, No. 21, pp. 2377–2380, XP–000166039, "Oxygen Optrode for Use in a Fiber–Optic Glucose Biosensor", 1990.

* cited by examiner

Primary Examiner—Jeffrey Snay
(74) Attorney, Agent, or Firm—Oblon, Spivak, McClelland, Maier & Neustadt, P.C.

(57) ABSTRACT

A method for detecting fluorescence from a liquid sample housed in a transparent or translucent sample container includes providing a sample container in a sample holder, which is opaque except for a sample container introduction opening and incoming and outgoing openings for excitation light; layering a liquid sample and a shielding liquid unmixable therewith to prevent external light from entering through the sample container introduction opening; introducing excitation light from such a direction that the excitation light can irradiate the liquid sample before irradiating the shielding liquid; and detecting fluorescence, which emits in a direction of avoiding absorption by the shielding liquid.

3 Claims, 7 Drawing Sheets

FLUORESCENCE DETECTION METHOD CAPABLE OF MAKING MEASUREMENT UNDER EXTERNAL LIGHT

The present invention relates to a fluorescent detection system, which detects a fluorescent signal from a specific substance included in a sample and determines the quantity of the specific substance based on a volume of the detected fluorescent signal, in particular a fluorescence detection system, which is effective to carry out real-time monitoring (tracing changes in the volume of the fluorescent signal with time) on many samples in the field of clinical diagnosis wherein incubation at a certain temperature is required for, e.g., enzymatic reaction.

For example, in the case of carrying out real-time monitoring on the progress in generation of a fluorescent reaction product caused by enzymatic reaction, it is necessary to carry out fluorescence detection while incubating a sample (reaction liquid) at a certain temperature. In addition, many samples need to be simultaneously and rapidly dealt with in some cases as in the field of clinical diagnosis.

As systems proposed to solve the problems, there are scanning type fluorescence detection systems disclosed in JP-A-2000-088752, JP-A-2000-214090 and JP-A-2001-091463.

The scanning type fluorescence detection system disclosed in JP-A-2000-088752 is configured to have sample containers provided so as to spread along an arc, have the ring portion of a ring type optical guide provided so as to confront the sample containers in the vicinity of the sample containers with a partition plate being provided between the ring portion and the sample containers, and have the partition plate fixedly provided with an optical unit for excitation light and an optical unit for fluorescent light as shown in FIGS. 5A and 5B, whereby the partition plate, the optical unit for excitation light and the optical unit for fluorescent light are integrally rotated to individually pick up fluorescent signals and transmit the fluorescent signals to an optical sensor through the ring type optical guide.

The scanning type fluorescence detection system disclosed in JP-A-2000-214090 is configured to have sample containers provided so as to spread along a plurality of arcs, have the ring portion of a ring type optical guide provided so as to confront the sample containers with a partition plate being provided between the ring portion and the sample containers, and have the partition plate fixedly provided with an optical unit for excitation light and an optical unit for fluorescent light including at least one optical guide as shown in FIG. 6, whereby the partition plate, the optical unit for excitation light and the optical unit for fluorescent light are integrally rotated to individually pick up fluorescent signals and transmit the fluorescent signals to an optical sensor through the ring type optical guide.

The scanning type fluorescence detection system disclosed in JP-A-2001-091463 is configured to have sample containers provided so as to spread along an arc as shown in FIGS. 7A and 7B, have a partition plate fixedly provided with a small-sized excitation light source, an optical unit for excitation light and an optical unit for fluorescent light in integrally rotatable fashion, and have the fluorescent light outgoing end of an optical guide of the optical unit for fluorescent light provided on the rotational center axis so as to confront an optical sensor, whereby fluorescent light from the respective sample containers is individually picked up for detection.

When the conventional fluorescence detection systems are utilized to carry out real-time monitoring on changes in fluorescent signals from a specific substance included in samples with time while incubating the samples at a certain temperature, the following problems have been raised.

When an excitation light source having a small size and a low output is utilized to make the entire system further smaller in each of the scanning type fluorescent detection systems of JP-A-2000-088752 and JP-A-2000-214090, the fluorescent signals become too feeble to provide sufficient sensitivity even in a supersensitive sensor, such as a photomultiplier. The reason is that the entrance of the ring type optical guide for transmission of fluorescent signals is normally as narrow as hundreds micrometer, causing the efficiency of fluorescent signals to lower. In particular, the scanning type fluorescence detection system of the JP-A-2000-214090 is likely to have insufficient sensitivity to extremely feeble fluorescent light since additional optical guides, which rotate, are provided in series with the stationary ring type optical guide to mediate the transmission of signals between the entrance and the ring type optical guide. Although the use of an excitation light source having a high output, such as an argon ion laser, can solve the insufficiency in sensitivity, a combination with a control source requires a large space, which is a bar to reduction in the physical size of the system.

Although the scanning type fluorescent detection system of JP-A-2001-091463 can solve the problem of reduction in the size, another problem is created when the number of samples to be simultaneously detected is large. The problem is caused by the followings: A reagent is added to many prepared samples one after another, and the samples with the reagent added thereto, and the samples are set in a conventional fluorescent detection system. In order to prevent external light from entering, the conventional fluorescent detection systems can not be operated until a shade cover is closed after the final sample has been set.

In particular, when the progress in incubation is rapid, a serious problem is raised. Specifically speaking, when the progress in incubation of samples is rapid, and when the number of samples to be simultaneously detected is large, it is become impossible to carry out real-time monitoring on the incubation since the incubation of a sample set at an early stage has been completed when the fluorescence detection system is operated. For this reason, even when the number of samples to be set in a single fluorescent detection system is determined as, e.g., n in design, there has been created a problem in that only far less than n number of samples can be used in practice.

This problem can be solved by eliminating the shade cover, which is provided in many fluorescence detection systems to cover the entire systems or all samples to be measured at one time for preventing external light from entering the fluorescence detection systems, or by enabling fluorescent measurement in an open state. Hereinbelow, the fluorescence measurement wherein the measurement is carried out without a shade cover for covering the entire system or all samples to be measured at one time is called "open fluorescence measurement" for convenience of explanation. A method for open fluorescence measurement is to provide shading caps for shading respective sample containers in a number equal to the number of the sample containers. However, when shading caps are provided to shade respective sample containers in a fluorescence detection system for measuring many samples, another problem, such as an increase in size and a cost rise, is created.

As explained, the fluorescence detection system for carrying our real-time monitoring on a fluorescent signal, in particular, carrying our real-time monitoring while incubating samples at a certain temperature needs to meet the requirements of, e.g., (a) temperature control with high accuracy, (b) rapid treatment of many samples, (c) high sensitivity, (d) high reliability (a reduce in mechanical trouble typified by disconnection or malfunction in movable parts, improvement in reproducibility of fluorescence detection, and a reduction in possibility of carry-over), (e) cost reduction (simplification in the structure of the system, and disuse of expensive parts for data treatment), and (f) a reduction in the physical size of the system, and further to realize (g) the open fluorescence detection to solve the problem deriving from a decrease in the incubation time.

It is an object of the present invention to provide a fluorescence detection method and a fluorescence detection system, which meet the requirements as stated above, in particular, to provide a system and a method for detecting fluorescence, which are effective to carry out real-time monitoring on many samples in rapid incubation fashion one after another, and which are capable of using a small-sized and supersensitive optical unit for fluorescence analysis to carry out the open fluorescence measurement.

The fluorescence detection method according to a first aspect of the present invention, which is provided to attain the object, is characterized in that the method for detecting fluorescence from a liquid sample housed in a transparent or translucent sample container comprises providing a transparent or translucent sample container in a sample holder, which is opaque except for a sample container introduction opening, an excitation light incoming opening and a fluorescence outgoing opening; layering a liquid sample and a shielding liquid unmixable therewith to prevent external light from entering through the sample container introduction opening; introducing excitation light from such a direction that the excitation light can irradiate the liquid sample before irradiating the shielding liquid; and detecting fluorescence, which emits in a direction of avoiding absorption by the shielding liquid.

The fluorescence detection method according to a second aspect of the present invention, which is provided to attain the object, is characterized in that the shielding liquid is made of oil with a shielding agent added thereto in the method according to the first aspect.

The fluorescence detection method according to a third aspect of the present invention, which is provided to attain the object, is characterized in that the shielding liquid is made of carbon black in the method according to the second aspect.

The fluorescence detection system according to a fourth aspect of the present invention, which is provided to attain the object, is characterized in that the fluorescence detection system comprises a sample holder for firmly holding a plurality of sample containers so as to be spread and held along an arc; a partition plate coupled to a drive unit so as to be rotatable about a center of the arc; an excitation light source, an optical unit for excitation light and an optical unit for fluorescence, which are fixedly provided to the partition plate so as to be integrally rotatable; and an optical sensor, which is fixedly provided in mechanically independent fashion with respect to the rotatable drive unit; wherein (a) excitation light intensity from the excitation light source is modulated so as to have a constant frequency;

(b) the optical unit for excitation light is provided so as to selectively excite a single sample container by directing excitation light from the excitation light source to the selected sample container;

(c) the optical unit for fluorescence includes an optical guide for transmitting a fluorescent signal from the selected sample container to the optical sensor, an incoming end of the optical guide can be provided so as to confront the selected sample container with the excitation light being directed thereto to pick up the fluorescent signal, and an outgoing end of the optical guide can be provided so as to confront the optical sensor on a center of rotation of the drive unit;

(d) the excitation light is directed to the respective sample containers spread along the arc one after another by rotation of the partition plate, and simultaneously fluorescence is directed to the optical sensor through the optical unit for fluorescence including the optical guide; and (e) an electrical signal outputted from the optical sensor is phase-detected by a modulated frequency of excitation light intensity.

The fluorescence detection system according to a fifth aspect of the present invention, which is provided to attain the object, is characterized in that the optical unit for excitation light is fixedly provided to the partition plate so as to selectively excite a single sample container by directing the excitation light from the excitation light source from beneath in an upward direction, and the optical unit for fluorescence is fixedly provided to the partition plate so as to pick up a fluorescent signal advancing from the sample container toward the center of rotation of the partition plate in a substantially horizontal direction in the fourth aspect.

The fluorescence detection system according to a sixth aspect of the present invention, which is provided to attain the object, is characterized in that the system according to the fourth aspect or the fifth aspect further comprises a thermostatic unit for controllably setting a sample at a desired temperature.

IN THE DRAWINGS

FIGS. 4A and 4B are schematic views showing the fluorescence detection system with a thermostatic unit provided thereto, wherein FIG. 4A is an enlarged view of the thermostatic unit (2:1), and FIG. 4B is a front view (partly in section);

FIGS. 5A and 5B are schematic view showing the entire structure of the fluorescence detection system according to an embodiment of the present invention, wherein FIG. 5A is a plan view, and FIG. 5B is a front view (partly in section);

Now, fluorescence detection system according to the present invention will be described in detail in reference to the accompanying drawings.

Figure 1:
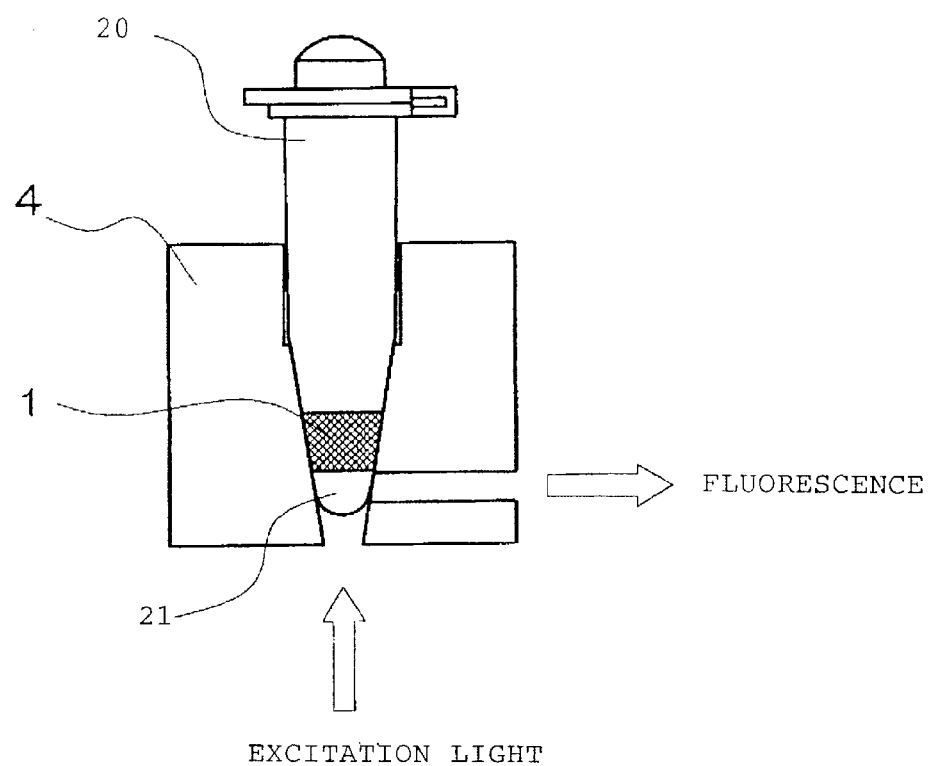
FIG. 1 is a schematic view showing the fluorescence detection method according to an embodiment of the present invention.

FIG. 1 schematically shows the fluorescence detection method according to an embodiment in the first through third aspects, which can carry out the open fluorescence measurement.

This is a fluorescence detection method wherein liquid samples, which are housed in respective transparent or translucent sample containers, are put in an opaque sample holder, and the respective liquid samples and a shielding liquid unmixable therewith are layered to prevent external light from entering into sample container introduction openings, thereby enabling the open fluorescence measurement to be carried out.

The sample holder is made of an opaque material except for the sample container introduction openings, incoming openings for excitation light and outgoing openings for fluorescence. For example, there is proposed a way to mold the sample holder from aluminum alloy and subject the molded holder to anodized aluminum treatment so as to have a black surface. The sample container introduction openings may be formed in any shape as long as the openings have an enough size to accept a sample container and can always firmly hold the sample container at a constant location.

The incoming openings for excitation light may be formed at any position in the sample holder as long as the incoming openings are located and oriented such that excitation light can irradiate the liquid samples before irradiating the shielding liquid. On the other hand, the outgoing openings for fluorescence may be formed at any position in the sample holder as long as the openings are located and oriented such that the openings can take out fluorescence, which has advanced in a direction of avoiding absorption by the shielding liquid. As long as both requirements are met, the incoming direction of the excitation light and the outgoing direction of the fluorescence may be in substantial alignment with each other. It is preferable that the incoming direction of the excitation light and the outgoing direction of the fluorescence make angles near to 90° with each other. For example, it is proposed to direct one of the incoming direction of the excitation light and the outgoing direction of the fluorescence toward a downward direction with respect to the liquid sample and to direct the other toward a horizontal direction with respect to the liquid sample.

The shielding liquid may be of any kind of liquid as long as the liquid can absorb light of all wavelengths in the excitation light that disturbs fluorescence measurement, and as long as the liquid is not unmixable with the liquid sample. The shielding liquid may be absorb external light on its own or may be prepared by adding a shielding agent to a proper liquid. The liquid samples are of an aqueous type in usual cases. In the usual cases, it is proposed to use an oil type liquid as the liquid unmixable with the liquid samples. For example, it is proposed to prepare the shielding liquid by adding carbon black to a mineral oil. In particular, the toner that is used in laser printers or copying machines comprises carbon black coated with polyethylene type or polystyrene type resin. Although the toner can properly disperse in an oil phase, the toner can not change to a aqueous phase. As other shielding agents, paint, pigment and magnetic fluid is applicable.

Figure 2:
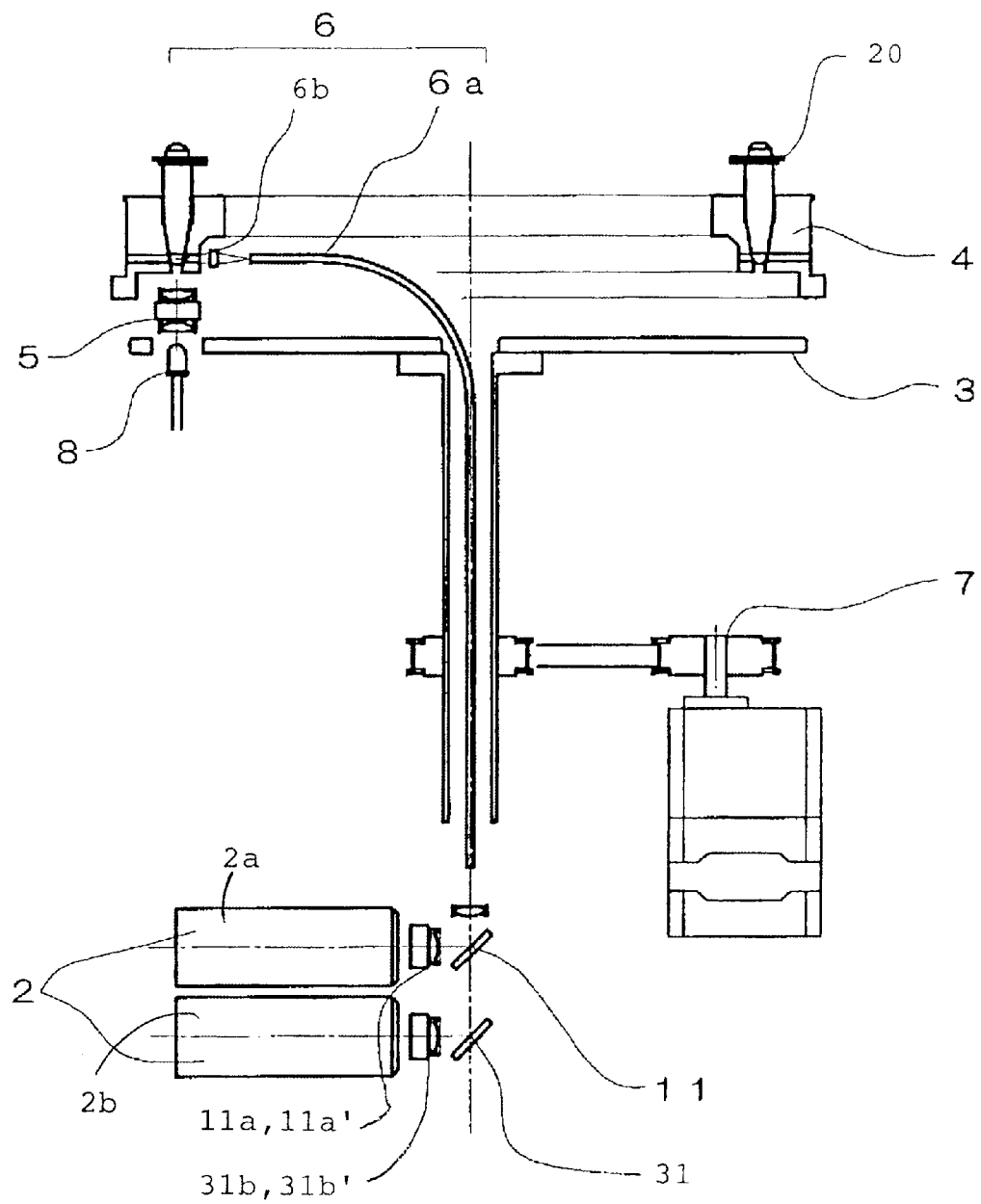
FIG. 2 is a schematic view showing the fluorescence detection system according to an embodiment of the present invention.

FIG. 2 schematically shows the fluorescence detection system according to an embodiment in the fourth and fifth aspects, which is effective to carry out the open fluorescence measurement in real-time monitoring on many firmly held samples, and which utilizes a small-sized and supersensitive optical unit for fluorescence analysis.

The sample holder 4 has holding holes formed along an arc so as to be fitted to the external shape of the respective sample containers 20. The sample containers with a sample 21 housed therein are firmly held in the sample holder so as to be spread along the arc. The sample containers, which are spread along the arc, are not necessarily located at equal intervals as shown and may be located at unequal intervals. There is no limit to the number of the sample containers to be firmly held in the sample holder. The number of the sample holders may be determined based on the length of the arc, the external diameter of the sample containers and other factors. The sample holder does not necessary have an upper side formed in a circular shape and may have the upper side formed in a polygonal shape, such as a square shape.

There is no limit to the material of the sample containers as long as the sample containers are made of a material that can pass excitation light and fluorescence therethrough and is chemically stable to samples to be housed therein. The material of the sample containers may be properly selected and used in consideration of the amount of samples subjected to fluorescence detection. In particular, when reaction progress in so-called PCR or NASBA is monitored while nucleic acid is enzymatically amplified, it is preferable to use sample containers with a sealing cap in terms of the purpose of preventing the amplified nucleic acid from scattering.

Under the firmly provided sample holder, a partition plate 3 is provided so as to be rotatable about the center of the arc with the sample containers spread thereon by being coupled with a drive unit 7. The partition plate is fixedly provided with an excitation light source 8, an optical unit for excitation light 5 and an optical unit for fluorescence 6, and these members can be integrally rotated by the drive unit 7.

It is preferable that the partition plate 3 comprises a disc to stabilize the rotational movement. The size (radius) of the partition plate is determined so as to be longer than at least the distance between the sample containers and the center of the arc so that the excitation light source 8, the optical unit for excitation light 5 and the optical unit for fluorescence 6 explained in detail later can be provided thereon. However, only the location of the partition plate where the optical unit for excitation light explained in detail later is fixedly provided is formed with a circular hole to pass excitation light through the partition plate. It is preferable that the partition plate is provided under the sample holder. The reason is that the amount of samples is as small as tens $\mu l$ in usual cases, and that the provision of the excitation light source, the optical unit for excitation light and the optical unit for fluorescence becomes easier in the usual cases since a fluorescent signal can be picked up from a position in the vicinity of the bottom of the sample containers.

Although the excitation light source 8 can be selected in consideration of the excitation wavelength of the samples, the excitation light source needs to be one wherein the excitation light that has reached a single sample container through the optical unit for excitation light 5 has a sufficient amount of light. From the viewpoint that the excitation light source is fixedly provided to the partition plate, it is preferable that the excitation light source is as small as possible. Specifically, examples of the excitation light source are a light emitting diode and a semiconductor laser. In the example shown in FIG. 2, a light emitting diode is used.

The optical unit for excitation light 5, which is fixedly provided to the partition plate, is one that works to select excitation light in terms of wavelength with respect to the light emitted from the excitation light source 8 and to selectively direct the excitation light to a single sample container among the sample containers, which are spread along the arc. In the example shown in FIG. 2, an interference filter is used for the wavelength selection to converge the excitation light on the specified sample container through an optical lens. The phrase "direct the excitation light to a single sample container" is not to be interpreted in a strict sense. It is sufficient that the excitation light can be directed to a single sample container as expected. For example, no problem is created even if a small amount of excitation light reaches another sample container by reflection on the external wall of that single sample container.

The optical unit for fluorescence 6, which is fixedly provided to the partition plate, is one that includes at least one optical guide 6a and performs such a function that only the fluorescence emitted from the single sample container, which the excitation light is directed to as stated earlier, is transmitted to an optical sensor 2. From this reason, the optical guide 6a has an fluorescence incoming end and a fluorescence outgoing end provided so as to confront the specific sample container and the optical sensor, respectively. Of course, a converging unit for the purpose of improving fluorescence transmission efficiency, such as an optical lens, and a wavelength selection unit for making a selection on the fluorescence wavelength may be interposed between the targeted sample container and the fluorescence incoming end of the optical guide. A similar converging unit or a similar wavelength selection unit may be interposed between the fluorescent signal outgoing end of the optical guide and the optical sensor. In the example shown in FIG. 2, the converging unit 6b is interposed between the targeted sample container and the fluorescence incoming end of the optical guide, and the converging unit and the wavelength selection unit are interposed between the fluorescent signal outgoing end of the optical guide and the optical sensor.

The fluorescent signal outgoing end of the optical guide 6a is provided on the rotational axis of the drive unit 7, which the partition plate is coupled to. By this arrangement, even when the partition plate 3 or the drive unit 7 rotates, fluorescent signals can be transmitted to the optical sensor with a constant efficiency since there is no change in the location of the fluorescent signal outgoing end of the optical guide. As the optical guide, it is the most appropriate to use a single optical fiber having considerable flexibility or a packed bundle of optical fibers wherein each of the optical fibers has both ends flush with both ends of the other optical fibers by use of proper fittings.

By adopting the arrangement stated earlier, the system shown in FIG. 2 can rotate the partition plate to direct the excitation light from the optical unit for excitation light to the respective sample containers fixedly held in the sample holder one after another. Additionally, the system can detect fluorescence emitted from the respective sample containers by the optical sensor through the optical unit for fluorescence including the optical guide. By accumulating the detection results obtained by the optical sensor with the rotation of the partition plate controlled by use of, e.g., a computer, the fluorescence direction results can be intermittently provided about the samples held in the sample holder to realize real-time monitoring.

Figure 3:
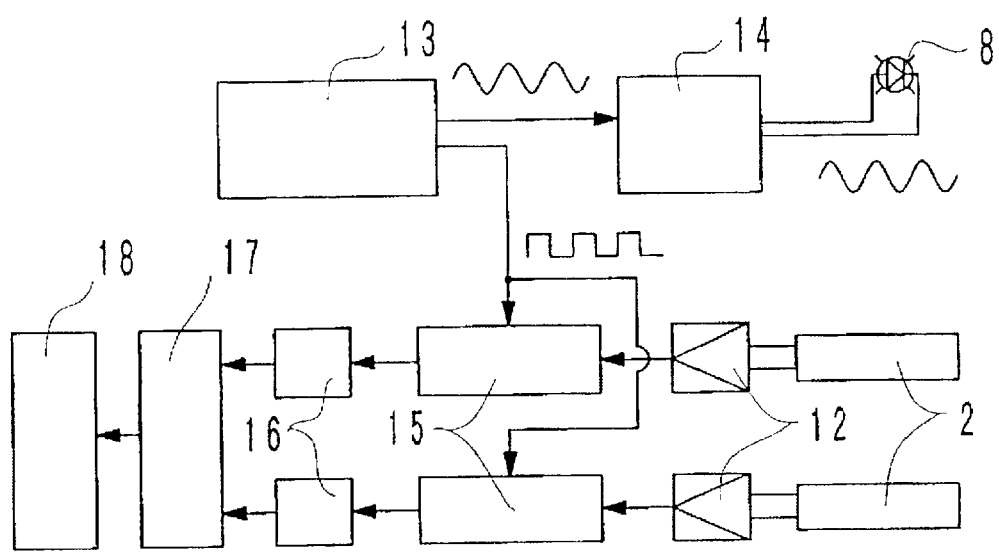
FIG. 3 is a block diagram explaining the modulation of excitation light and the phase-detection of a fluorescent signal in the fluorescence detection system.

In order to cope with the open fluorescence measurement, it is preferable to use both modulation of excitation light intensity and phase-detection of fluorescent signals as shown in FIG. 3. In particular, external light that passes through and enters a transparent or translucent container could create a problem in some cases since the fluorescence to be detected is feeble. A combination of the modulation and the phase-detection is effective in these cases. Specifically speaking, the light emitting diode of the excitation light source is pulse-oscillated, and electrical signals from the optical sensor are phase-detected at the frequency of the pulse by use of a lock-in amplifier. By this arrangement, only the fluorescent signals can be selectively detected among signals including external light.

Although the modulated excitation light intensity may have any waveform as long as the frequency and the wave height are stable, it is preferable to use a sinusoidal wave or a rectangular wave. The intensity of fluorescent signals are also modulated as in the intensity of the excitation light since the fluorescence intensity is proportional to the intensity of the excitation light. Although an electrical signal from the optical sensor contains both modulated fluorescent signal and signal of external light entering the system, it is possible to selectively pick up only the modulated fluorescent signal by a so-called lock-in amplifier to carry out phase-detection at the modulated frequency of the excitation light intensity. By this arrangement, it is possible to realize the open fluorescence measurement capable of detecting fluorescent signals in stable manner without being affected by the external light that enters the system in a minute amount.

Figure 4A:
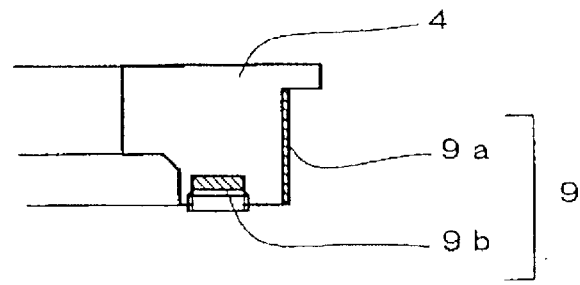
Figure 4B:
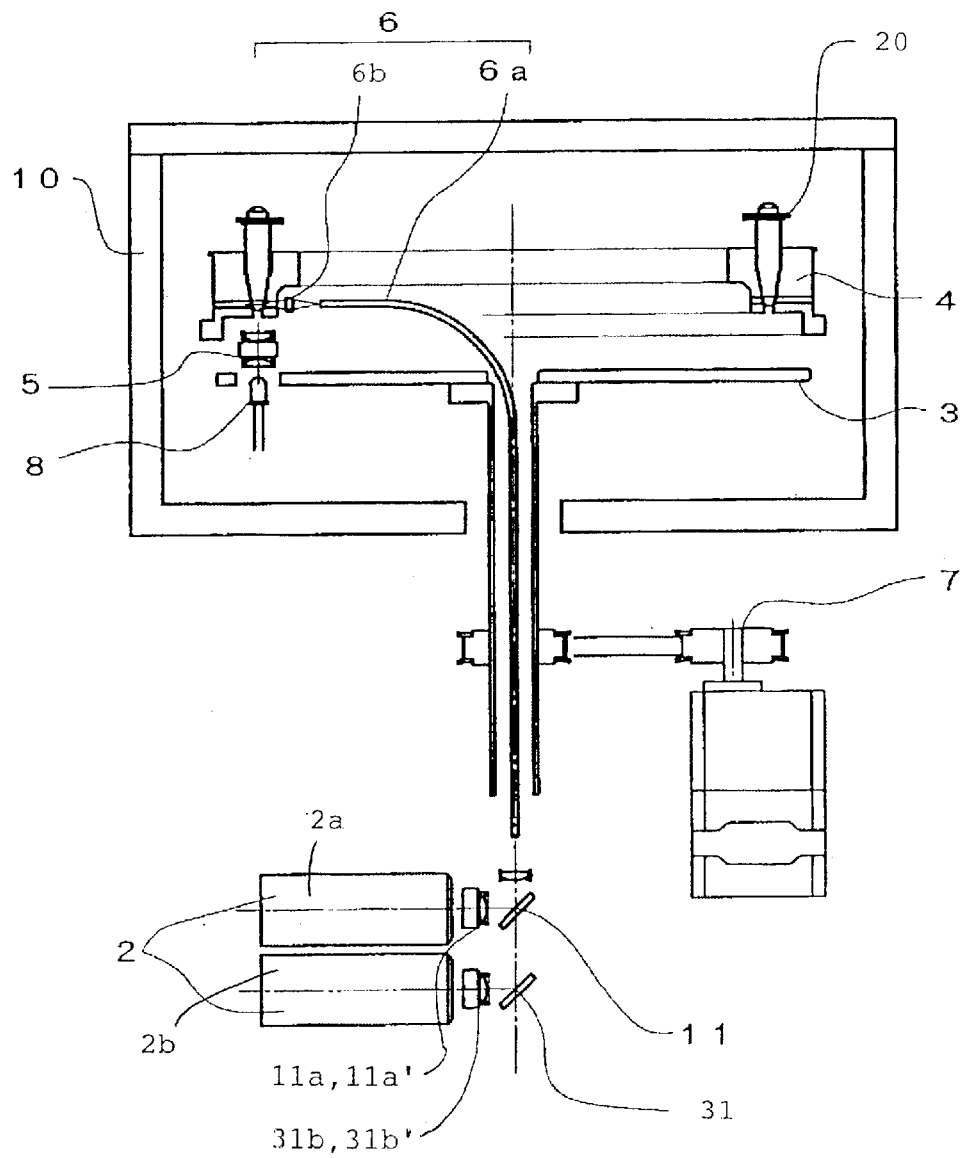

FIGS. 4A and 4B schematically show the fluorescence detection system with an incubation function provided by a thermostatic unit according to an embodiment in the sixth aspect, which is effective to carry out the open fluorescence measurement in real-time monitoring on many firmly held samples. Specifically speaking, the fluorescence detection system shown in FIGS. 4A and 4B is one wherein the optical unit for fluorescence analysis is provided with the thermostatic unit for controllably setting samples at a desired temperature.

The thermostatic unit 9 for controllably setting samples at a desired temperature utilizes a single heater 9a and a single temperature sensor 9b. The sample holder 4 has an upper side formed in an annular shape, the heater 9a is affixed to the outer peripheral of the sample holder, and the temperature sensor 9b is provided on an inner wall of the sample holder. By this arrangement, it is possible to controllably set samples at a desired temperature by heat-conduction from the sample holder.

In the example shown in FIGS. 4A and 4B, there is provided a heat-insulated enclosure 10, which accommodates almost all of the sample holder, the partition plate, the drive unit thereof, the excitation light source, the optical unit for excitation light and the optical unit for fluorescence fixedly provided to the partition plate, and a shielding plate. In order that the samples, which are subjected to the temperature control by the thermostatic unit, are insulated from an external temperature to carry out temperature control with higher accuracy, it is preferable to provide the heat-insulated enclosure. From the viewpoint that the heat-insulated enclosure is used for that purpose, it is sufficient that at least the sample holder is accommodated in the enclosure.

Of course, the thermostatic unit is not limited to the arrangement stated earlier. For example, it is acceptable to accommodate at least the sample holder in a constant temperature enclosure having a constant temperature therein to control the temperature of the sample holder by convection of, e.g., air. The thermostatic unit is not limited to the heating by use of, e.g., a heater. The temperature control may be provided by cooling or a heat cycle with heating and cooling repeated. In the case of cooling, a cooling element, such as a Peltier element or a cooling fan, may be used in place of the heater. In the case of the heat cycle, the cooling element, such as a Peltier element or a cooling fan, may be used in combination with a heating element, such as a heater.

By combining the optical unit for fluorescence detection shown in FIG. 2 and the thermostatic unit for samples as explained, it becomes possible to carry out incubation, such as enzymatic reaction, for many samples at a desired temperature with high accuracy and simultaneously to provide a fluorescence detection system capable of carrying out real-time monitoring on changes in fluorescent signals caused by enzymatic reaction with time.

Now, in order to describe the fluorescence detection system according to the present invention in further detail, an example will be explained in reference to FIG. 5A–FIG. 7B. The present invention is not limited to the example.

Figure 5A:
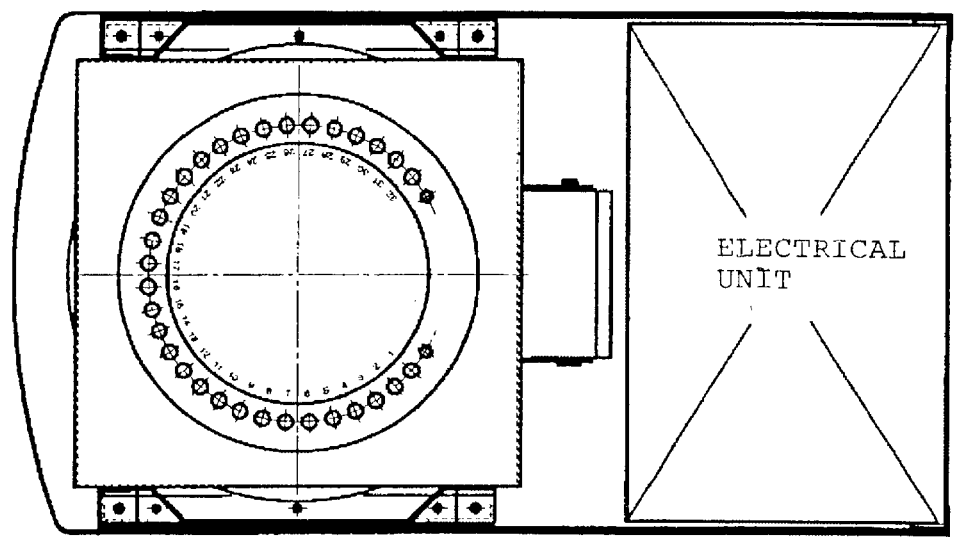
Figure 5B:
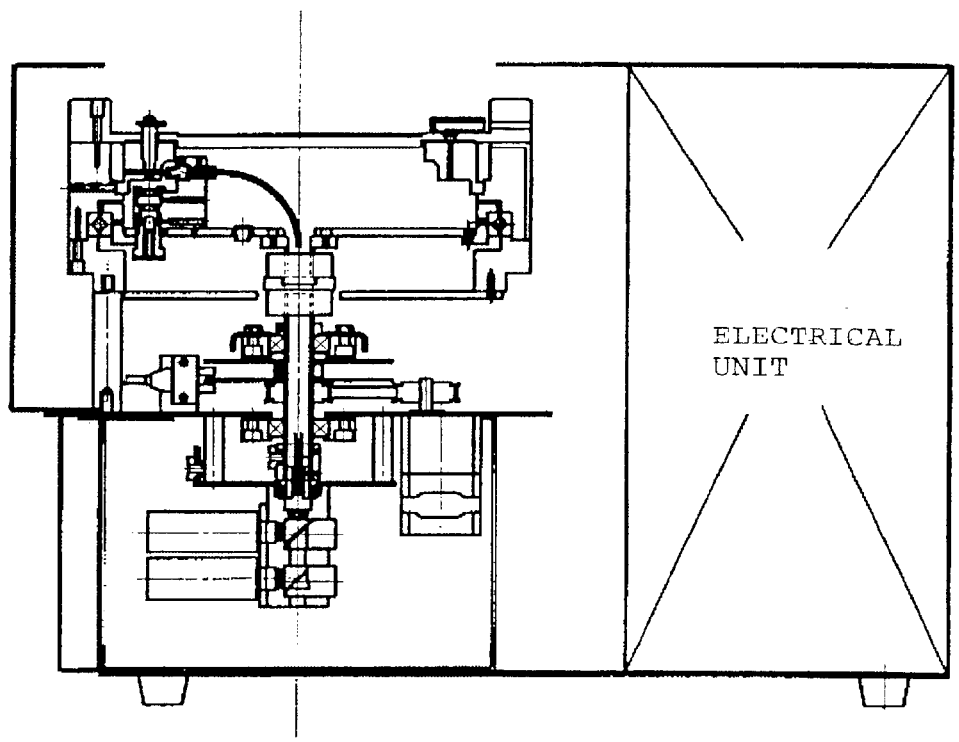
Figure 6:
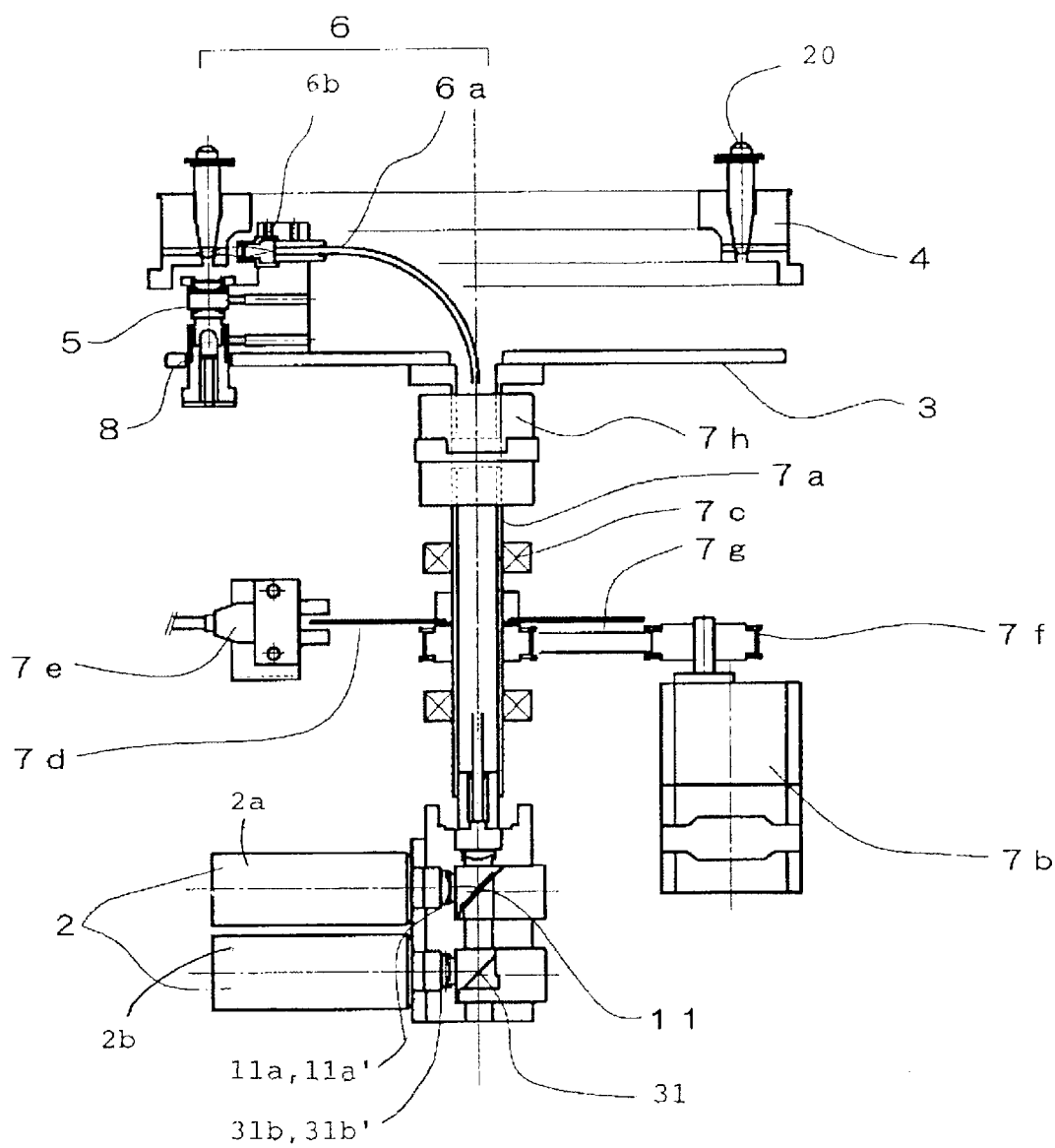
FIG. 6 is a front view explaining parts of the fluorescence detection system shown in FIG. 5 in detail, wherein some parts are shown in section.

As the fluorescence detection system capable of carrying out the open fluorescence measurement, the system shown in FIGS. 5A and 5B has been fabricated. The fluorescence detection system is the system referred to as the fourth, fifth and sixth aspects.

FIG. 5A–FIG. 7B are views explaining the fluorescence detection system according to the present invention in detail.

Figure 7A:
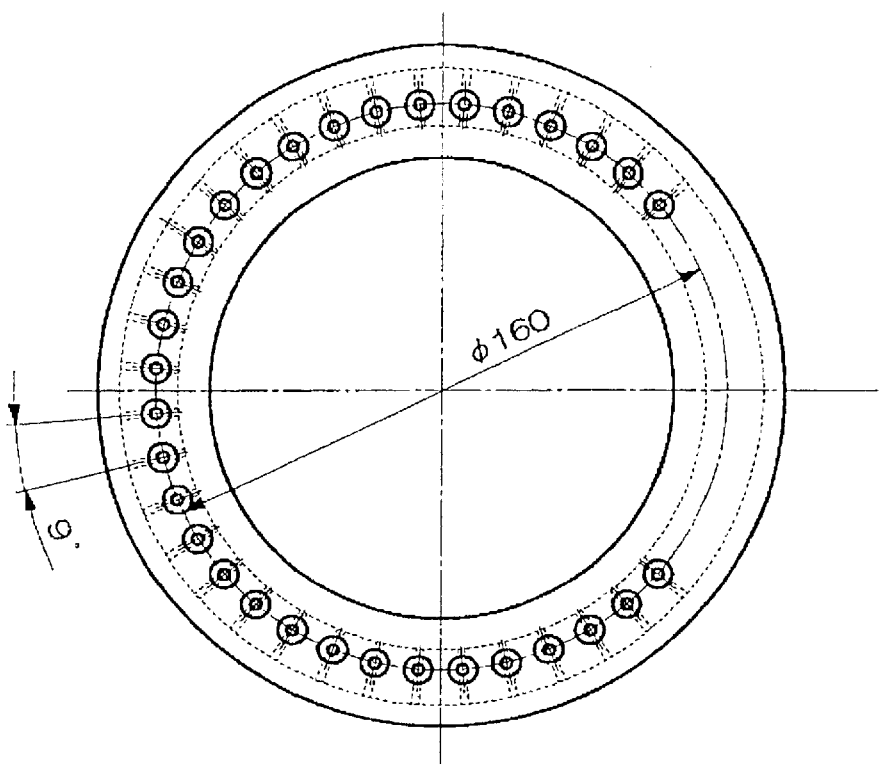
FIGS. 7A and 7B are a plan view and a front view in section explaining the sample holder and the thermostat unit of the fluorescence detection system shown in FIG. 6 in detail.
Figure 7B:
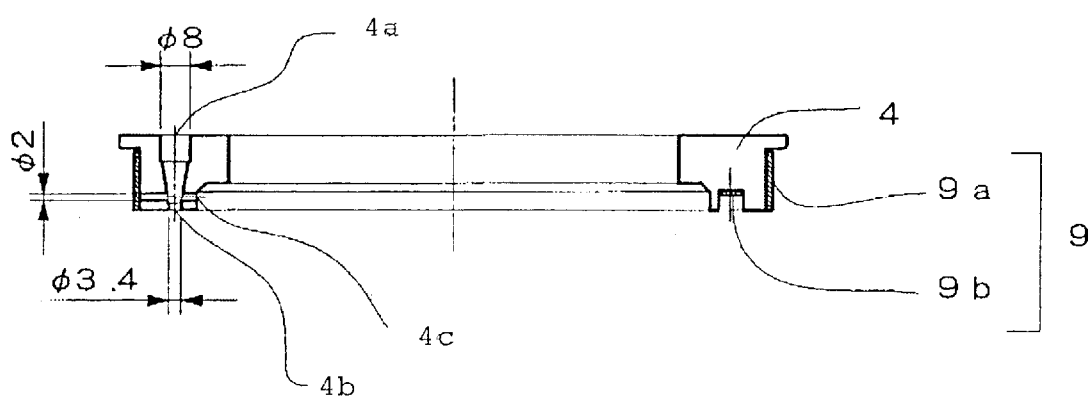

As shown in FIGS. 7A and 7B, a sample holder 4 has been made of an aluminum alloy member in an annular shape and has been formed with 32 holes for receiving and holding a sample container 4a, 32 holes for passing excitation light therethrough 4b and 32 holes for picking up fluorescence 4c. The holes for receiving and holding a sample container are holes fitted to the outer diameter of a sample container (the largest diameter is 8 mm), which have been provided in the sample holder so as to be spread along an arc having a diameter of 160 mm in equal intervals at a pitch of 9°. Each of the holes has had a lower inner portion formed in such a tapered shape to be fitted to the shape of a sample container for support of the bottom of the sample container in close fashion. Each of the holes for passing excitation light therethrough (a diameter of 3.4 mm) has been formed in a lower end of the annular aluminum alloy member so that each of the holes has a central axis in alignment with the central axis of the corresponding hole for receiving and holding a sample container. Each of the holes for picking up fluorescence (a diameter of 2 mm) has been formed in the aluminum alloy member so as to have a central axis perpendicular to the central axis of the corresponding hole for receiving and holding a sample container.

Under the sample holder has been provided a disc shaped partition plate 3. The partition plate 3 has had a peripheral portion distant from the center by 80 mm formed with a hole for passing a fluorescent signal, and fixedly provided with a light emitting diode as the excitation light source 8 (a central emission wavelength of 470 nm), an interference filter for wavelength selection as the optical unit for excitation light 5 (a transmission center wavelength 470 nm and a half bandwidth of 10 nm) and an optical lens for convergence. Additionally, the partition plate 3 is fixedly provided with, as the optical unit for fluorescence 6, two converging lens for fluorescence convergence 6b and an optical guide 6a, which is explained later. The optical unit for excitation light 5 and the optical unit for fluorescence 6 have been located so as to have the central axis of both units extending perpendicularly to each other. By this positional relationship, the fluorescence, which has been excited by the excitation light, can be picked up effectively.

As the optical guide 6a, which is one of the constituent elements of the optical unit for fluorescence 6 to transmit a fluorescent signal, a plastic optical fiber having a diameter of 2 mm has been used. The optical guide 6a have had a fluorescent signal incoming end fixedly positioned at the convergent point of the converging lenses so as to confront a sample container. The optical guide has been provided so as to extend through a rotational shaft 7a of a drive unit for the partition plate stated later, and the optical guide has had a fluorescent signal outgoing end fixedly provided to the rotational shaft at the rotational center so as to be located on the rotational center.

To the partition plate 3 has been coupled the drive unit 7, which comprises the rotary shaft 7a in a cylindrical shape, a stepping motor 7b, a bearing 7c, a rotary slit plate 7d, a rotational position sensor 7e, a timing pulley 7f, a timing belt 7g and a coupling 7h. By this arrangement, the partition plate 3 and the excitation light source 8, the optical unit for excitation light 5, the optical unit for fluorescence 6 and a shielding plate 12 fixed thereto have been integrally rotatable in response to the operation of the drive unit 7. By provision of the rotary slit plate and the rotational position sensor, it has become possible to detect the rotational position of the partition plate, i.e., the position of a sample container under fluorescence detection at each moment.

Ahead of the fluorescent signal outgoing end of the optical guide 6a has been provided a dichroic mirror as a wavelength dispersion unit 11 with an optical lens interposed therebetween for light path separation for different wavelengths with a separation boundary of about 560 nm. In the light path for the reflection light by the dichroic mirror (not longer than 560 nm) have been provided an optical filter for wavelength selection (interference filter: 520 nm) 11a, an optical lens 11a' and an optical sensor (photo-multiplier) 2a. On the other hand, in the light path for the transmission light through the dichroic mirror (longer than 560 nm) have been provided a total reflection mirror 31, an optical filter for wavelength selection (interference filter: 610 nm) 31b, an optical lens 31b' and an optical sensor (photo-multiplier) 2b. By this arrangement, fluorescent signals having a wavelength of 520 nm and a wavelength of 610 nm have been simultaneously detected, respectively.

These parts have been designed and assembled so as to be fixed by base boards, supporting rings, supporting members or other members in terms of mutual positional relationships.

The electrical unit shown in FIGS. 5A and 5B has included an electronic circuit, which works to pulse-oscillate the light emitting diode as the excitation light source at a constant frequency, and an electronic circuit, which works to phase-detect an electric signal from the optical sensor at the same frequency by use of a lock-in amplifier.

The modulated light emission from the light emitting diode 8 as the excitation light source has been carried out by using a drive circuit for excitation light source 14 to current-amplify a sinusoidal wave having a frequency of 1,590 Hz generated by a synchronizing signal generator 13. Additionally, the synchronizing signal generator has been made to generate a rectangular wave having the same frequency as the sinusoidal wave to use the rectangular wave as a reference signal input for lock-in amplifiers 15.

The electric signals from the optical sensors have been amplified by signal amplifier circuits 12, and then the amplified electric signals have been inputted to the lock-in amplifiers 15 to be phase-detected by the reference signal. By this arrangement, only fluorescent signals have been selectively detected among signals containing external light to eliminate the influence caused by the external light, which enters in a minute amount. After harmonic noise components have been eliminated from the phase-detected signals by low-pass filter circuits 16, the signals have been quantized by an analogue-to-digital converter 17 and have been digitalized by a signal processing/controlling circuit 18. The sample holder has had a heater 9a affixed to an outer peripheral portion thereof and a temperature sensor 9b provided therein. A tape-shaped heater has been used as the heater, and a resistance temperature sensor made of platinum has been used as the temperature sensor. The sample holder, the partition plate, some parts of the drive unit, the excitation light source, the optical unit for excitation light and the optical unit for fluorescence have been housed in a heat-insulated enclosure. The heat-insulated enclosure has been made of a material having a small heat conductivity, such as polyacetal type plastics or foamed polyethylene. With samples being heat-insulated from external environment as explained, the samples have been temperature-controlled with high accuracy to provide the system with an integration function, such as enzymatic reaction.

The fluorescence detection system explained above detects fluorescent signals from the samples under the following operation. The excitation light emitted from the light emitting diode excites, from beneath through the optical unit for excitation light, the sample in a sample container, which is received and held in the sample holder. The fluorescence emitted by the sample is emitted from a side portion of the sample holder toward the rotation center of the partition plate and is transmitted by the optical unit, such as the optical guide, which is provided to the partition plate. The fluorescence transmitted by the optical guide is subjected to light path separation by the wavelength dispersion unit, and the reflection light and the transmission light are selected by the interference filter having a wavelength of 520 nm and the interference filter having a wavelength of 610 nm in terms of wavelength, respectively. After that, the reflection light and the transmission light are converted into electric signals by the photo-multipliers and are detected.

Since the 32 sample containers are firmly provided and spread along the arc, the rotation of the partition plate causes the excitation by the excitation light and the fluorescence collection by the optical unit for fluorescence to be carried out from one sample container to another sample container. This means that it is possible to easily carry out the fluorescence detection for many samples (32 samples in this embodiment). By reversely rotating the partition plate to return the partition plate to the original rotational position after completing the fluorescence measurement for the 32 samples, and repeating the operation stated earlier, it becomes possible to intermittently monitor the progress of changes in the fluorescence signals of the samples with time.

When the system was actually utilized to detect fluorescence, a shielding liquid was prepared. The shielding liquid was prepared as an oil type since aqueous type samples were used. Specifically, carbon black of 50 mg/ml was mixed with mineral oil. As the carbon black, toner for laser printers was used. When the fluorescence detection was carried out, the liquid sample of 25 $\mu$l was poured into each of sample containers, the shielding liquid of 100 $\mu$l was poured into each of the sample containers with the liquid sample therein, and the sample containers were set in the sample holder.

In accordance with the fluorescence detection system according to the present invention offers the following advantages.

Since the sample holder, which can hold a plurality of sample containers, is fixedly provided, temperature control can be carried out with high accuracy with respect to the respective samples housed in the sample containers, whereby many samples can be dealt with rapidly. Additionally, since the sample containers are firmly provided without being conveyed, it is possible to eliminate the danger of causing a temperature difference among samples during conveyance or carry-over due to vibration or joggle during conveyance.

Even if the system is provided with the thermostatic unit, the system can carry out signal detection with high sensitivity since the optical sensor can be provided outside of the thermostatic unit to prevent noise from increasing due to a raise in temperature. In addition, it is possible to reduce the costs since a single optical sensor is utilized for a single wavelength. It is also possible to eliminate a troublesome operation for sensitivity compensation with respect to the respective sensors, which are essential when the system is made smaller, or when a plurality of optical sensors are utilized for a single wavelength. Further, the load for data processing can be made lighter since it is possible to see changes in fluorescence signals with time with respect to many samples by dealing with signals from a single optical sensor with respect to a single wavelength. In particular, when a photo-multiplier is conveniently utilized as the optical sensor, it is possible to provide the fluorescence detection system with extremely high sensitivity. This arrangement can have sufficient sensitivity to a feeble fluorescent signal.

There is no change in the bent form of the optical guide since the optical guide is fixedly provided to the partition plate and rotates while keeping the same form. As a result, there is no change in light transmission efficiency caused by a change in the bent form of the optical fiber, and as a consequence, it is possible to carry out signal detection with good reproducibility.

In the system according to the present invention, the mechanically movable parts are limited to the partition plate and the parts fixedly provided thereto, and the mechanically movable parts are subjected to simple rotational movement. As a result, the mechanical trouble can be restrained to the minimum. As explained, the present invention can realize real-time monitoring for many samples by rotating the partition plate and the optical units, though the present invention carries out neither conveyance nor movement of sample containers.

The problem of insufficient sensitivity, which is created when a small-sized and low output excitation light source is used in a scanning type fluorescence detection system disclosed in, i.e., JP-A-2000-088752 or JP-A-2000-214090, can be solved by using a single optical guide as the transmission member for a fluorescence signal. In the embodiment stated earlier, the effective output of the light emitting diode used as the excitation light source is actually about 1/40 times smaller than the argon ion laser used in JP-A-2000-088752 or JP-A-2000-214090. However, the present invention can realize fluorescence detection with substantially the same sensitivity as that of JP-A-2000-088752 or JP-A-2000-214090. Additionally, the present invention can offer cost reduction since a ring type optical guide can be eliminated.

Further, the open fluorescence measurement, which has been demanded in the conventional fluorescence detection systems including the detection system disclosed in JP-A-20001-091463 and the conventional fluorescence detection method using the detection systems, can be carried out. Even when the progress in incubation is rapid, many samples can be subjected to real-time monitoring one after another.

As explained, the present invention provides a fluorescence detection system and a fluorescence detection method, which meet the requirements the requirements of, e.g., (a) temperature control with high accuracy, (b) rapid treatment of many samples, (c) high sensitivity, (d) high reliability (a reduce in mechanical trouble, improvement in reproducibility of fluorescence detection, and a reduction in possibility of carry-over), (e) cost reduction (simplification in the structure of the system, and disuse of expensive parts for data treatment), and (f) a reduction in the physical size of the system, and further to realize (g) the open fluorescence detection to solve the problem deriving from a decrease in the incubation time.

The entire disclosure of Japanese Patent Application No. 2001-124172 filed on Apr. 23, 2001 including specification, claims, drawings and summary are incorporated herein by reference in its entirety.

What is claimed is:

1. A method for detecting fluorescence from a liquid sample housed in a transparent or translucent sample container, comprising:

providing a transparent or translucent sample container in a sample holder, which is opaque except for a sample container introduction opening, an excitation light incoming opening and a fluorescence outgoing opening;

layering a liquid sample and a shielding liquid unmixable therewith to prevent external light from entering through the sample container introduction opening;

introducing excitation light from such a direction that the excitation light can irradiate the liquid sample before irradiating the shielding liquid; and detecting fluorescence, which emits in a direction of avoiding absorption by the shielding liquid.

2. The method according to claim 1, wherein the shielding liquid is made of oil with a shielding agent added thereto.

3. The method according to claim 2, wherein the shielding liquid is made of carbon black.

* * * * *